US007754243B2

United States Patent
Sun

(10) Patent No.: US 7,754,243 B2
(45) Date of Patent: Jul. 13, 2010

(54) AQUEOUS SUSPENSION OF NANOSCALE DRUG PARTICLES FROM SUPERCRITICAL FLUID PROCESSING

(75) Inventor: Ya-Ping Sun, Clemson, SC (US)

(73) Assignee: Clemson University Research Foundation, Anderson, SC (US)

( * ) Notice: Subject to any disclaimer, the term of this patent is extended or adjusted under 35 U.S.C. 154(b) by 1021 days.

(21) Appl. No.: 10/910,786

(22) Filed: Aug. 3, 2004

(65) Prior Publication Data

US 2006/0029676 A1 Feb. 9, 2006

(51) Int. Cl.
*A61K 9/14* (2006.01)
(52) U.S. Cl. .................................................. 424/489
(58) Field of Classification Search ........................ None
See application file for complete search history.

(56) References Cited

U.S. PATENT DOCUMENTS

| | | | |
|---|---|---|---|
| 4,734,227 A | 3/1988 | Smith | |
| 5,360,478 A | 11/1994 | Krukonis et al. | |
| 5,389,382 A * | 2/1995 | List et al. ................. | 424/499 |
| H1839 H | 2/2000 | Combes et al. | |
| 6,177,103 B1 * | 1/2001 | Pace et al. ................. | 424/489 |
| 6,299,906 B1 | 10/2001 | Bausch et al. | |
| 6,451,963 B1 | 9/2002 | Langel et al. | |
| 6,479,708 B1 | 11/2002 | Jacobson et al. | |
| 6,576,264 B1 | 6/2003 | Henriksen et al. | |
| 6,660,176 B2 | 12/2003 | Tepper et al. | |
| 6,682,761 B2 | 1/2004 | Pace et al. | |
| 6,974,593 B2 * | 12/2005 | Henriksen et al. ........... | 424/490 |
| 2002/0000681 A1 | 1/2002 | Gupta et al. | |
| 2002/0081334 A1 | 6/2002 | Johnston et al. | |
| 2002/0119916 A1 | 8/2002 | Hassan | |
| 2003/0003070 A1 * | 1/2003 | Eggers et al. ............... | 424/70.1 |
| 2003/0041602 A1 | 3/2003 | Williams, III et al. | |
| 2003/0045597 A1 | 3/2003 | Randolph et al. | |
| 2003/0059465 A1 * | 3/2003 | Unger et al. ................ | 424/465 |
| 2003/0077329 A1 | 4/2003 | Kipp et al. | |
| 2004/0009229 A1 | 1/2004 | Unger et al. | |
| 2004/0022861 A1 | 2/2004 | Williams, III et al. | |

FOREIGN PATENT DOCUMENTS

| WO | WO 9714407 A1 | 4/1997 |
|---|---|---|
| WO | WO 9952504 A1 * | 10/1999 |
| WO | WO 9965469 A2 | 12/1999 |

OTHER PUBLICATIONS

Search Report and Written Opinion for PCT/US05/27508, Jul. 25, 2006.
Article—*Drug Delivery Applications of Supercritical Fluid Technology*, Gangadhar Sunkara, M. Pharm, and Uday B. Kompella, Drug Delivery Technology, Supercritical Fluids, vol. 2, No. 1, 2002, 10 pages.
Article—*Preparation of Budesonide and Budesonide-PLA Microparticles Using Supercritical Fluid Precipitation Technology*, Todd M. Martin, Nagesh Bandi, Ryan Schulz, Christopher B. Robers, and Uday B. Kompella, AAPS PharmSciTech, vol. 3, 2002, 11 pages.
Article—*Rapid Expansion from Supercritical to Aqueous Solution to Produce Submicron Suspensions of Water-Insoluble Drugs*, Timothy J. Young, Simon Mawson, and Keith P. Johnston, Biotechnol. Prog. vol. 16, 2000, pp. 402-407.
Article—*Supercritical-Fluid Processing Technique for Nanoscale Polymer Particles*, Mohammed J. Meziani, Pankaj Pathak, Razvan Hurezeanu, Mark C. Thies, Robert M. Enick, and Ya-Ping Sun, Angew. Chem. Int. Ed., vol. 43, 2004, pp. 704-707.
Chapter entitled *Preparation and Processing of Nanoscale Material by Supercritical Fluid Technology* from book entitled *Supercritical Fluid Technology in Material Science and Engineering* by Ya-Ping Sun, Jayasundera Bandara, Jaouad M. Meziani, Harry W. Rollins, and Christopher E. Bunker, 2002, pp. 491-576.
Paper—Editor's Choice/Highlights of the Recent Literature, Science, vol. 303, Feb. 13, 2004, 2 pages.

* cited by examiner

*Primary Examiner*—S. Tran
(74) *Attorney, Agent, or Firm*—Dority & Manning, P.A.

(57) ABSTRACT

The present invention is directed to an improved supercritical fluid processing technique that can be used to form particulate suspensions of biologically useful materials. The disclosed processes include variations of RESS processes. The disclosed processes do not form micelles of any stabilizing agents in the aqueous solution that receives the product materials following rapid expansion through a nozzle. In particular, stabilizing agents in the aqueous solution are either materials that will not form micelles in aqueous environments, or else they are materials that can form micelles, but are utilized at conditions that are insufficient for the formation of micelles or at least not suitable for any significant presence of micelles in the product. Through utilization of the disclosed process, particulate suspensions can be formed exclusively of very small particles, for example, particulate suspensions in which all of the particles formed are less than 100 nm in size. Moreover, the product suspension of particles can be very homogeneous, with particle size distribution standard deviations of less than about 15 nm.

7 Claims, 3 Drawing Sheets

Fig. 3A
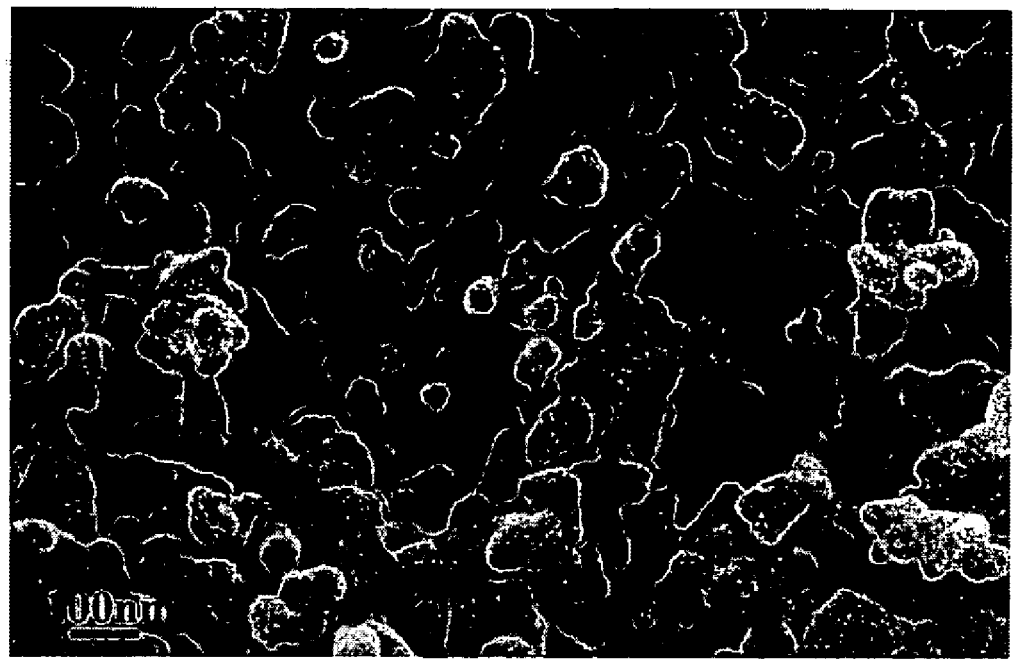
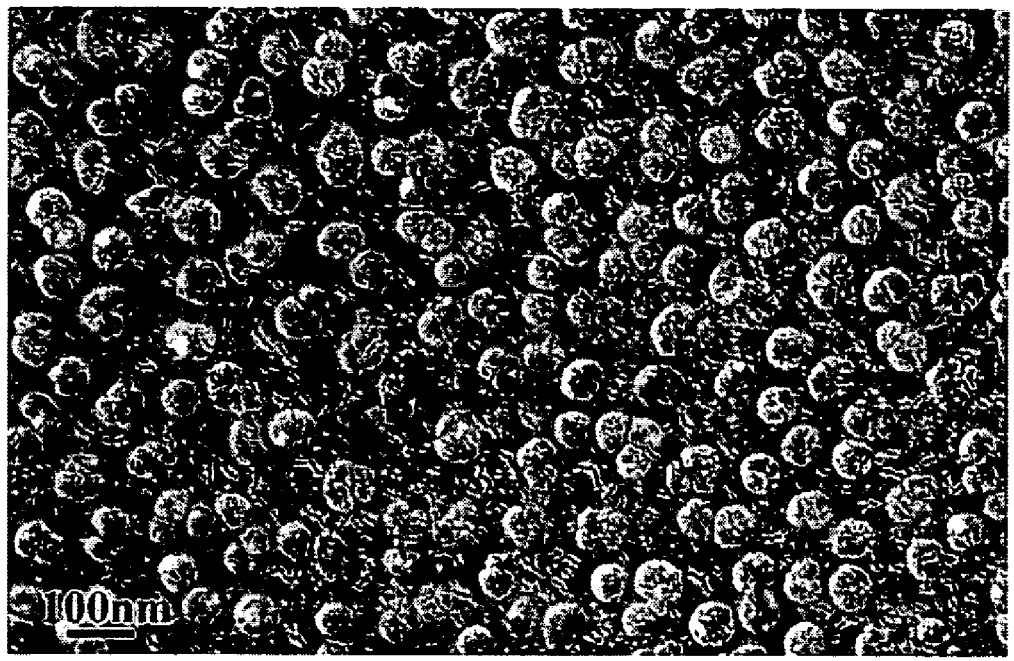
Fig. 3B

AQUEOUS SUSPENSION OF NANOSCALE DRUG PARTICLES FROM SUPERCRITICAL FLUID PROCESSING

BACKGROUND OF THE INVENTION

Many materials useful in the treatment or diagnosis of disease are not soluble in water or other water-based solvent systems, which presents difficulties when attempting to administer such materials to people or animals. As a result, many processes have been designed and a great deal of research has been carried out to try and solve this insolubility problem and prepare these materials in a form in which they may be readily administered to and utilized by biological systems. For example, mechanically grinding or milling the materials has been attempted, as has chemically altering the materials with hydrophilic derivatives and thus increase the solubility of the materials. These methods have met with limited success and have often, particularly in the case of derivatization processes, proven costly. Moreover, derivatization of materials can introduce questions as to efficacy of the products due to the chemical alterations necessary to improve solubility.

It has been generally recognized that a suspension of nanoscale (i.e., less than 100 nm in size) materials is generally equivalent to a solution of the same materials when considered for medical applications such as the treatment or diagnosis of disease. As such, one approach to solving the insolubility problem of many biologically active materials has been directed toward the development of technologies that can produce suspensions of nanoscale materials.

Supercritical fluid processing techniques have shown promise in the production of micron- and submicron-sized (less than 1 µm) particles of water-insoluble materials, and in particular in regard to drug particles. For example, U.S. Pat. No. 6,576,264 to Henriksen, et al., and U.S. Pat. No. 6,177,103 to Pace, et al. describe processes that can generate submicron particles of biologically useful materials through the use of supercritical or compressed fluid processing techniques. Unfortunately, neither of these patented processes solves the insolubility problem of the materials, as both patents disclose processes that form particle suspensions including primarily or at least a substantial portion of drug particles over 100 nm in size. Suspensions that include a large percentage of particles larger than 100 nm in size are disadvantageous for medical applications due to, for instance, difficulties with intravenous delivery, slower dissolution rate (and thus slower system absorption), increased toxicity, lower intracellular uptake, shorter retention in tumor tissue, increased MPS (mononuclear phagocytic system) uptake, shorter circulating capacity in the blood, and lower stability against enzymatic degradation (especially for protein, peptide, and nucleic acid drugs). Drug particles greater than 100 nm in size can also be too large to penetrate into tissues through fine capillaries such as the liver sinusoidal.

In addition, these patents utilize phospholipids and surfactant materials during the disclosed processes and form micelles of these materials in the product suspension. As such, the aqueous suspensions as formed are believed to include empty micelles as well as drug particles within or in some physical combination with the micelle-forming materials. As such, the purity of the formed suspensions can be less than optimal. Moreover, the presence of the micelle-forming materials in the products could also interfere with the efficacy of the drugs.

What is needed in the art are improved methods for forming stable suspensions of nanoscale particles of biologically useful materials. In particular, what is needed in the art are methods for forming high purity, stable suspensions of nanoscale particles of biologically active materials with a very small size distribution among the particles held in the suspension.

SUMMARY OF THE INVENTION

In one embodiment, the present invention is directed to a method for forming an aqueous suspension of biologically active materials. The method can include dissolving a biologically active material that displays little or no aqueous solubility into a suitable solvent to form a non-aqueous solution. In one particular embodiment, the solvent can be carbon dioxide.

In some embodiments, the non-aqueous solution can also include a co-solvent to aid the dissolution of the material. For instance, the co-solvent can be present in an amount that is less than about 10% by weight or by volume of the non-aqueous solution.

Following formation, the non-aqueous solution can be compressed and heated to form a supercritical solution and can be rapidly expanded through a nozzle into an aqueous solution. Upon rapid expansion of the supercritical solution, a particulate suspension can form in the aqueous solution. In particular, the particles formed in the suspension can be particles of the biologically active material that are very homogeneous in size. For example, the particle size distribution standard deviation of all of the particles formed in the aqueous solution can be less than about 15 nm. In one embodiment, the particle size distribution standard deviation of all of the particles formed in the aqueous solution can be between about 5 nm and about 10 nm.

The product suspension can also include very small particles. For example, in one embodiment, at least 95% of the particles formed according to the disclosed process can be less than 100 nm in diameter. In one embodiment, the disclosed process can form exclusively particles less than 100 nm in size.

The aqueous solution into which the supercritical solution is expanded can contain a biologically compatible stabilizing agent. Importantly, the stabilizing agent does not form micelles in the aqueous solution. For example, the stabilizing agent can, in one embodiment, be a material that does not form micelles in an aqueous environment. In another embodiment, the stabilizing agent may be capable of forming micelles in an aqueous environment, but is in the aqueous solution in a concentration of less than the critical micelle concentration (CMC) of the material or under conditions that are not suitable for any significant presence of micelles, and as such, does form micelles in the product suspension.

The stabilizing agents of the disclosed process can be present in the aqueous solution in a relatively low amount as compared to the biologically active material. For instance, the ratio of biologically active material to stabilizing agent can be greater than 1:1, for example, between about 1:1 and about 4:1. In one embodiment, this ratio can be between about 2:1 and about 4:1.

In one particular embodiment, the stabilizing agent can be a food emulsifier. Other possible stabilizing agents can include certain surfactants, water-soluble proteins, such as bovine serum albumin, oleic acid, poly(vinyl alcohol), poly (lactic acid), poly(glycolic acid), poly(methylidene malonate 2.1.2), and poly(alkyl cyanoacrylates).

The product suspensions formed according to the present invention can be very stable. For example, the particulate suspension can be stable at ambient temperature. In addition, the particulate suspension can be formed and stable at physiological pH.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which:

FIG. 3A is an SEM image of Naproxen nanoparticle samples obtained utilizing neat water as the aqueous receiving material;

FIG. 3B is an SEM image of Naproxen nanoparticle samples obtained utilizing a PVP solution as the aqueous receiving material;

Figure 1:
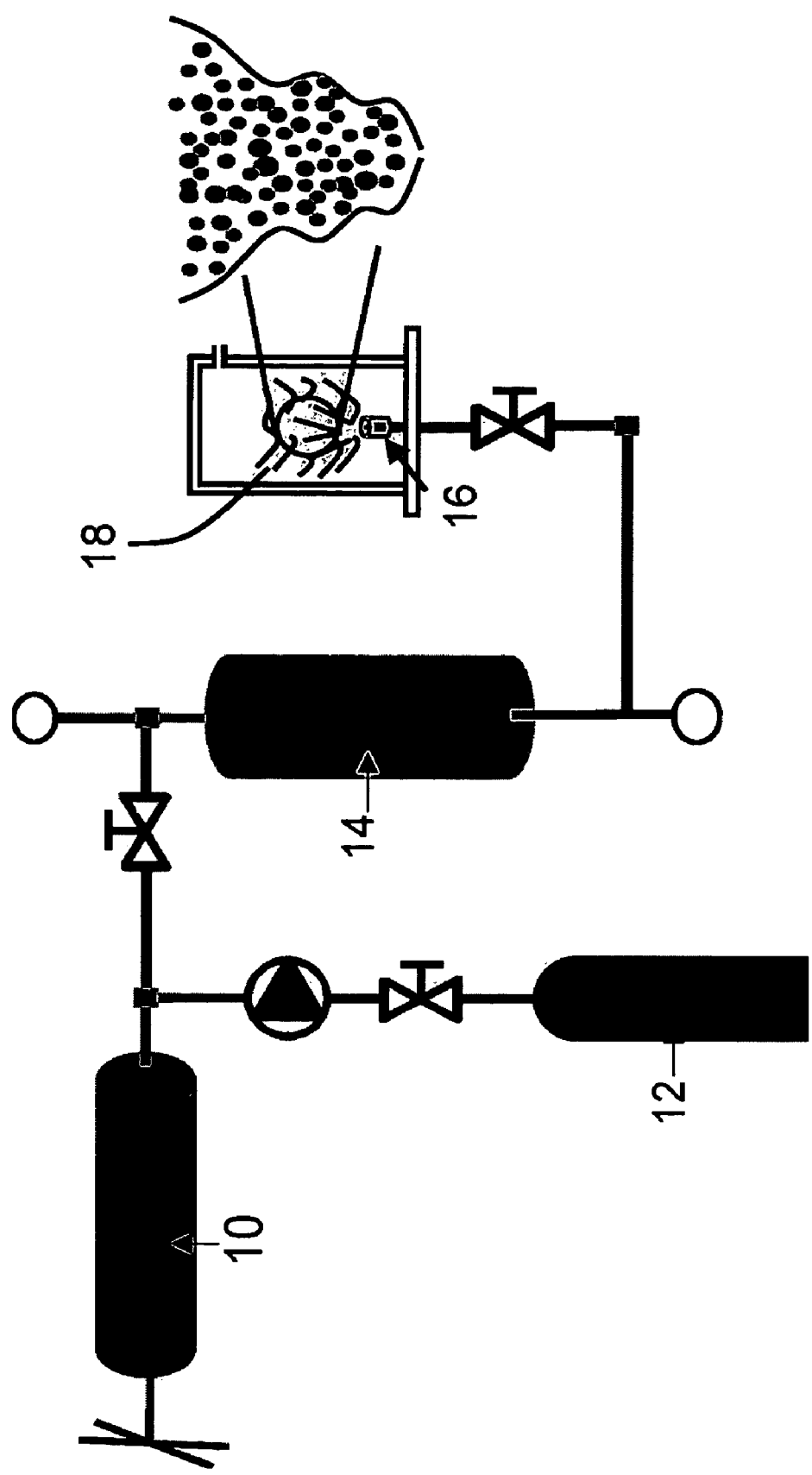
FIG. 1 is a schematic diagram illustrating one embodiment of the disclosed process.

Repeat use of reference characters in the present specification and drawings is intended to represent the same or analogous features or elements of the present invention.

DETAILED DESCRIPTION OF THE INVENTION

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment. Thus, it is intended that the present invention cover such modifications and variations as come within the scope of the appended claims and their equivalents.

In one embodiment, the present invention is directed to methods for producing stable aqueous particulate suspensions of biologically useful materials having no or poor aqueous solubility. In general, the methods are based upon known supercritical fluid processes and include modifications of the conventional Rapid Expansion of Supercritical Solution (RESS) process. More particularly, the processes of the present invention include the formation of a supercritical solution of the biologically active materials. The supercritical solution can then be rapidly expanded into an aqueous solution to precipitate particles of the biologically active materials. In addition, the aqueous solution can contain stabilizing agents that can prevent the agglomeration of the precipitated particles and thus encourage the formation of the particles in the desired size range with a narrow size distribution. Moreover, utilizing the disclosed processes, the product suspensions can have a very high purity with regard to the biologically active materials due to the low amounts of stabilizing agents necessary in the process.

More particularly, the particulate suspensions formed according to the disclosed processes can contain primarily or, in some embodiments, exclusively, particles less than 100 nm in size. In addition, the formed particles can have a very narrow size distribution. For instance, the suspended particles can have an average size of between about 10 and about 65 nm with a size distribution standard deviation of less than about 10 nm. In one embodiment, the particles in the suspension can have an average diameter of about 40 nm and a size distribution standard deviation of less than 10 nm. Moreover, the suspensions of the invention can be formed so as to contain only particles of the biologically active materials, with no extraneous particles or micelles in the products that do not include the biologically active materials of interest.

In addition, the products suspensions of the present invention can have a pH in physiological range upon formation and can be stable at physiological pH and ambient temperature. Beneficially, as the stabilizing agents of the process are generally biocompatible, in most embodiments of the process there is no need for any post-formation separation techniques to remove non-compatible materials from the product suspension. Consequently, many post processing techniques and special storage conditions necessary for product suspensions formed according to previously known processes are no longer necessary in many embodiments of the disclosed invention.

According to the presently disclosed process, a variation of the Rapid Expansion of Supercritical Solution process can be utilized to form the product suspensions. In particular, a biologically active material of interest can first be dissolved in a supercritical fluid to form a supercritical solution. Referring to FIG. 1, one embodiment of the disclosed process is schematically illustrated. According to this embodiment, the solvent and the biologically active material of interest can be combined in a high-pressure generator such as a syringe pump 10.

Biologically active materials of interest in the present invention are generally materials that display little or no aqueous solubility, i.e., less than about 5 mg/mL water at a pH of about 6.5 to about 7.4. Of course, the water solubility may be even less, for instance less than 1 mg/mL in some embodiments, or lower yet, for instance, in some embodiments less than about 0.1 mg/mL. In particular, materials of interest can include organic and/or polymeric biologically active materials including, for example, pharmaceutically useful materials such as materials for treatment or prevention of human or animal disease, imaging agents, diagnostic agents, materials being tested for possible biological activity and/or utility, and the like.

A non-limiting list of exemplary classes of biologically active materials that may be of interest in the present invention can include analgesics, antagonists, anti-inflammatory agents, anthelmintics, antianginal agents, anti-arrhythmic agents, antibiotics (including penicillins), anticholesterols, anticoagulants, anticonvulsants, antidepressants, antidiabetic agents, antiepileptics, antigonadotropins, antihistamines, antihypertensive agents, antimuscarinic agents, antimycobacterial agents, antineoplastic agents, antipsychotic agents, immunosuppressants, antithyroid agents, antiviral agents, antifungal agents, anxiolytic sedatives (hypnotics and neuroleptics), astringents, beta-adrenoceptor blocking agents, blood products and substitutes, anti-cancer agents, cardiacinotropic agents, contrast media, corticosteroids, cough suppressants (expectorants and mucolytics), diuretics, dopaminergics (antiparkinsonian agents), haemostatics, immunosuppressive and immunoactive agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anorexics, sympathomimetics, thyroid agents, vasidilators, neuron blocking agents, anticholinergic and cholinomimetic agents, antimuscarinic and muscarinic agents, vitamins, and xanthines.

According to the disclosed process, the biologically active material can be dissolved in a suitable solvent, generally a compressed gas in the supercritical or sub-critical fluid phase, though the phase of the solvent at this stage is not a requirement of the invention. In the field of physical chemistry, and for purposes of this disclosure, the term critical fluid refers to a substance at or above its critical temperature and at or above its critical pressure. The term supercritical fluid (SCF) refers to a substance above its critical temperature and above its critical pressure. The term "near critical" is used in the sense of approaching or close to being critical. For example, a substance having a temperature below its critical temperature and a pressure at or above the critical pressure may be considered a near critical fluid. Such a substance can have properties that may approach those of a supercritical or critical fluid, particularly in solvating properties.

The solvent utilized in the disclosed process can generally be any of a number of liquefied compressed gases known to the art. These include but are not limited to gaseous oxides such as carbon dioxide and nitrous oxide; alkanes such as ethane, propane, butane, and pentane; alkenes such as ethylene and propylene; alcohols such as ethanol and isopropanol; ketones such as acetone; ethers such as dimethyl or diethyl ether; esters such as ethyl acetate; halogenated compounds including sulfur hexafluoride, chlorofluorocarbons such as trichlorofluoromethane (Freon 11, $CCl_3F$,), dichlorofluoromethane (Freon 21, $CHCl_2F$), difluorochloromethane (Freon 22, $CHClF_2$), and fluorocarbons such as trifluoromethane (Freon 23, $CHF_3$); and elemental liquefied gases such as xenon. Optionally, the solvent can include mixtures of one or more suitable materials. In general, the biocompatibility of the solvent is not an issue in the disclosed process, as the supercritical solution will generally separate completely post-expansion, with the gas leaving the system or being collected for recycling and the solute forming the nanoparticles in the product aqueous suspension.

In one particular embodiment of the present invention, carbon dioxide can be utilized as the solvent in forming the supercritical solution. For example, in certain embodiments wherein the solute is a nonpolar material, carbon dioxide can be utilized as the solvent without the necessity of including any modifier to the solution, such as a cosolvent, for instance. Supercritical $CO_2$ can be preferred in other embodiments as well, however, even when the solubility of the solute is not particularly high in the solvent, due to the nature of $CO_2$ as well as the obvious economic advantages of using the material. In particular, $CO_2$ has a near-ambient critical temperature (about 31° C.) and a relatively low critical pressure (73.8 bar). It is also non-toxic, non-flammable, abundant and inexpensive.

Referring again to FIG. 1, according to one embodiment, the solvent can be conveniently stored in a cylinder 12, and then pumped to the syringe pump 10 to be combined with the solute. Optionally, one or more modifiers, e.g., co-solvents or other modifiers, may also be included in the syringe pump 10 to aid the formation of the supercritical solution. In general, in those embodiments utilizing a co-solvent, only small amounts of co-solvent need be used, for instance less than about 10% by weight or volume of the SCF solution. In one embodiment, a SCF solution can comprise less than about 5 wt % co-solvent. In another embodiment, a SCF solution can comprise less than about 2 wt % co-solvent.

Preferably, any modifiers included with the supercritical solution can be biologically compatible materials, so as to negate the necessity of any post-formation removal procedures. This is not a requirement of the invention, however. For example, a non-limiting list of exemplary co-solvents can include methanol, ethanol, acetone, ethyl acetate, and DMSO, which form homogeneous mixtures with supercritical $CO_2$ at moderate temperatures and pressures and are miscible with water. Miscibility of a co-solvent with water is necessary in the present invention, due to the aqueous nature of the receiving solution, similar to traditional precipitation and condensation processes. Following formation of the product suspension, any co-solvent or other modifier remaining in the product can be removed, if desired, according to standard processes as are generally known in the art. For example, a co-solvent can be removed from the product suspension by dialysis of the sample with water.

Following the combination of the solvent, the biologically active material, and any modifiers in the syringe pump 10, the mixture can be conveyed under pressure through a pre-heated heating unit 14 to form the supercritical solution. For instance, in one embodiment, the heating unit 14 can be a tube furnace including a solid block of high heat capacity material, such as copper, wrapped in a coil of stainless steel tubing. Any suitable heating unit 14 can optionally be utilized, however.

Depending primarily upon the solvent used, in some embodiments it may be preferable to pre-heat the syringe pump 10 as well as the heating unit 14. For example, in those embodiments wherein the solvent has a relatively high critical temperature, it may be preferred to pre-heat the syringe pump 10 to ensure the solution reaches the designated temperature by the exit of the heating unit 14 and that it becomes thermally equilibrated before rapid expansion through an expansion nozzle 16.

The expansion nozzle 16 can be any suitable expansion nozzle as is generally known in the art. For example, the expansion nozzle 16 can be a specifically designed and constructed micro-orifice. In one embodiment, expansion nozzle 16 can be a fused-silica capillary held within stainless steel tubing. In general, the expansion nozzle 16 can have an internal diameter of between about 1 and about 100 µm and an aspect ratio (L/D) of at least about 5.

The expansion nozzle 16 can be inserted into an expansion chamber 18 containing an aqueous receiving solution. To prevent the premature precipitation of the biologically active material and clogging of the nozzle 16, the nozzle 16 can optionally be heated to the pre-expansion temperature.

In accord with the present invention, the aqueous receiving solution includes a stabilizing agent. In particular, the stabilizing agents of the present invention do not form micelles in the aqueous solutions. For instance, in one embodiment, the stabilizing agent can be a water-soluble material that does not form micelles in an aqueous solution. In another embodiment, the stabilizing agent can be a material that can form micelles, but is at a low concentration in the receiving solution in relation to the concentration of the biologically active material. In particular, the stabilizing agent is at a concentration such that the material does not form any significant micelles in the product suspension. In those embodiments including the utilization of one or more stabilizing agents that can form micelles in aqueous solution, the concentration of the stabilizing agents is such that, even if the agents can form micelles when in pure water, upon introduction of other materials, e.g., the biologically active material, the receiving solution will not include any significant presence of micelles. In one embodiment, the concentration of stabilizing agents that can form micelles in aqueous solution can be less than the CMC of those particular materials. Table 1, below, lists the CMC of some possible stabilizing agents of the present invention.

TABLE 1

| Stabilizing Agent | MW | CMC (mM) |
|---|---|---|
| Triton X-100 | 628 | 0.24 |
| Triton X-114 | 537 | 0.21 |
| Brij-35 | 1225 | 0.09 |
| Brij 58 | 1120 | 0.077 |
| Brij 76 | 710 | 0.003 |
| Brij 97 | 710 | 0.94 |
| Tween-20 | 1228 | 0.06 |
| Tween-80 | 1310 | 0.012 |
| Sodium Dodecyl Sulfate | 288 | 6-8 |
| AOT (sodium bis(2-ethylhexyl)-sulfosuccinate) | 444 | 2.5 |

In any case, according to the presently disclosed process, the stabilizing agent will be at a relatively low concentration as compared to the amount of biologically active material in the product suspension. In particular, the ratio of the biologically active material to stabilizing agent in the product suspension can be greater than that found in previously known RESS processes and modifications thereof. For example, in one embodiment, the ratio of biologically active material to stabilizing agent in the receiving solution can greater than about 1:1. In one embodiment, this ratio can be between 1:1 and about 4:1. In one embodiment, this ratio can be between about 1.5:1 and about 4:1. In another embodiment, this ratio can be between about 2:1 and about 4:1.

While not wishing to be bound by any particular theory, it is believed that in the present invention, the amounts and types of the disclosed stabilizing agents in the receiving solution can provide a physical barrier to prevent the agglomeration of the suspended nanoscale particles of biologically active materials. In particular, and in contrast to previously known processes, it is not necessary for the stabilizing agents to be of a type and in a quantity so as to ensure coating and/or encapsulation of the formed particles. Moreover, it is believed that use of the disclosed stabilizing agents can encourage the formation of a product suspension of nanoscale particles of biologically active materials in which the particles are very homogeneous in size.

The ability to utilize low amounts of stabilizing agents in the receiving solution and still prevent agglomeration of the biologically active materials can provide other benefits to the disclosed invention as well. For example, the utilization of less stabilizer can improve efficiency and decrease costs associated with the processes. In addition, the product suspensions can be formed with very high purity in regard to the amount of the biological active material in suspension when compared to other components in the aqueous suspension. For example, in one embodiment, and excluding the amount of water, the aqueous product suspension can be at least about 50% biologically active material as formed. In another embodiment, the aqueous product suspension as formed can be at least about 60% biologically active material, excluding water. In another embodiment, the aqueous product suspension can be at least about 80% biologically active material as formed.

The lack of formation of micelles in the receiving solution is believed to offer other advantages to the presently disclosed process as well. For example, the disclosed process can be simple and easily sized to enable mass production, as no special processing steps are required to keep the stabilizing agents in the aqueous solution from agglomerating excessively. For instance, strong agitation or homogenization of the receiving solution is not necessary prior to or during the rapid expansion of the SCF. In addition, all of the particles formed by the process can contain the biologically active material. In other words, the product suspension formed according to the disclosed process will not contain any empty micelles, as is the case in other particle suspension forming processes that include the formation of micelles in a product solution. In many previously known SCF processes for forming nanoparticle suspensions, there tended to be particles of two distinct classes in the suspension, one class being micelles of phospholipids or other micelle-forming surfactants, and a second class of particles that include the desired drug particles, possibly combined with the surfactants. This problem has been obviated in the disclosed process.

Stabilizing agents that can be utilized in the present invention can include polymers and biopolymers that are generally not considered surfactants, water-soluble proteins, as well as certain surfactant materials. In one embodiment, surfactants that can be utilized in the disclosed process include surfactant materials that do not form micelles in aqueous solution. In another embodiment, surfactants that can form micelles in aqueous environments can be utilized, but in this particular embodiment, the materials can be used at low concentrations, for instance at concentrations near or below the CMC, as previously discussed.

Examples of some suitable surfactants that can be utilized in the disclosed process include certain natural surfactants, such as casein, tragacanth, waxes, enteric resins, paraffin, acacia, gelatin; nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose; anionic surfactants such as potassium laurate, triethanolamine stearate, sodium lauryl sulfate, alkyl polyoxyethylene sulfates, sodium alginate, dioctyl sodium sulfosuccinate, and negatively charged glyceryl esters, sodium carboxymethylcellulose, and calcium carboxymethylcellulose; cationic surfactants such as quaternary ammonium compounds, benzalkonium chloride, cetyltrimethylammonium bromide, and lauryldimethylbenzyl-ammonium chloride; colloidal clays such as bentonite and veegum or a combination thereof.

Other stabilizing agents that can be utilized in the disclosed process can include polaxomers, such as PLURONIC™ F68, F108 and F127, and poloxamines, such as TETRONIC.™ 908 (T908), available from BASF, TRITON™ X-200, available from Rohm and Haas, hydroxy propyl methylcellulose, dimyristoyl phosphatidylglycerol sodium salt, sodium dodecyl sulfate, sodium deoxycholate, and cetyltrimethylammonium bromide.

In another embodiment, stabilizing agents of the present invention can include both traditional and novel stabilizing agents for small particle-formation and related systems, for example, oleic acid, citric acid, poly(vinyl alcohol), poly (lactic acid), poly(glycolic acid), poly(methylidene malonate 2.1.2), poly(alkyl cyanoacrylates), polymers and biopolymers that are not generally considered surfactants. In one embodiment food emulsifiers can be utilized as stabilizing agents in the disclosed invention. A non-limiting exemplary list of suitable stabilizing agent food emulsifiers can include partial glycerides, such as mono- and diglycerides, lactic acid esters of monoglycerides, acetic acid esters of monoglycerides, and citric acid esters of monoglycerides; fatty acid esters of polyols, including propylene glycol esters of fatty acids, polyglycerol esters of fatty acids, sorbitan esters, and the like; ethoxylated emulsifiers, such as ethoxylated partial glycerides and polysorbates; phosphatides, such as lecithin; phosphorylated partial glycerides, such as phosphorylated monoglyceride; and sodium strearoyl-lactylate.

In another embodiment, stabilizing agents of the present invention can include water-soluble proteins. For example bovine serum albumin, ferritin and the like.

Upon rapid expansion of the SCF into the receiving solution, the biologically active material can nucleate and crystallize to form the product suspension. Unlike the traditional RESS process, in which a supercritical solution is expanded into air or vacuum, the aqueous receiving solution of the present invention is believed to suppress the particle growth in the expansion jet and promote the formation of particles less than 100 nm in diameter. Of importance, the formation of the small nanoparticles in the presently disclosed process is not disturbed or interfered with due to excessive stabilizing agents, and in particular, micelle-forming materials in the solution. Moreover, due to the utilization of stabilizing agents, but stabilizing agents of a type and/or in a concentration to ensure that micelles will not form in the product suspension, the product suspension can remain stable over a long period of time, up to several weeks or months, in some embodiments.

In addition, the products of the present invention can be very homogenous suspensions of extremely small particles as formed, with no additional separation steps, such as filtration, for example, necessary to obtain the desired product suspension. In particular, the particle suspensions of the present invention as formed can include particles of biologically active material that are all very small, small enough to be easily taken up and distributed throughout a biological system. In addition, the particles of the suspension need not be derivatized with any functional groups that could confuse or alter the efficacy of the biologically active materials. For instance, in one embodiment, at least about 95% of the particles of biologically active material in the product suspension as initially formed can be less than 100 nm in diameter. In one particular embodiment, the product suspension as formed can include exclusively nanoscale particles, that is, exclusively particles less than 100 nm in diameter. In one embodiment, the diameter of all of the biologically active particles in the suspension as formed can be between about 10 and about 95 nm. In one embodiment, the average diameter of all of the biologically active particles in the suspension as initially formed can be between about 10 and about 50 nm.

In addition, the particles of the product suspension can also be very homogenous in size, that is, the formed particles can have a small size distribution standard deviation. For example, the size distribution standard deviation of all of the particles formed according to the process can be less than about 15 nm. In one embodiment, the particle size distribution standard deviation of all of the formed particles can be between about 5 and about 10 nm. In another embodiment, the size distribution standard deviation can be between about 5 and about 8 nm.

Moreover, the product suspensions of the present invention can be very stable as formed. For example, the product suspensions of the invention can be stable at room temperature, i.e., no special temperature conditions are required for storage of the product suspensions. In addition, according to the present invention, the product suspensions can be formed in physiological range (about 6.5 to about 7.4) and no special pH control or manipulation is necessary prior to use of the product suspension.

The present invention may be better understood with reference to the following examples:

EXAMPLE 1

A system similar to that illustrated in FIG. 1 was utilized to form aqueous suspensions of Ibuprofen particles. Specifically, a solution (0.25 mg/mL) of Ibuprofen (available from Sigma-Aldrich Corporation) in liquid carbon dioxide (high-purity, SFC grade obtained from Air Products Corporation) was prepared in the syringe pump 10. The solution was pushed through the heating unit 14 to reach the desired supercritical temperature of 40° C. before reaching the expansion nozzle 16. The rapid expansion was carried out at a pre-expansion pressure of 200 bar through a 50 μm orifice into an aqueous solution.

A specimen of the product suspension was prepared for SEM imaging by depositing a few drops of the dilute nanoparticle aqueous suspension onto a carbon tape, followed by drying under ambient condition and then coating with platinum before imaging. SEM images were obtained on a Hitachi S-4700 Field-Emission SEM system.

Figure 2A:
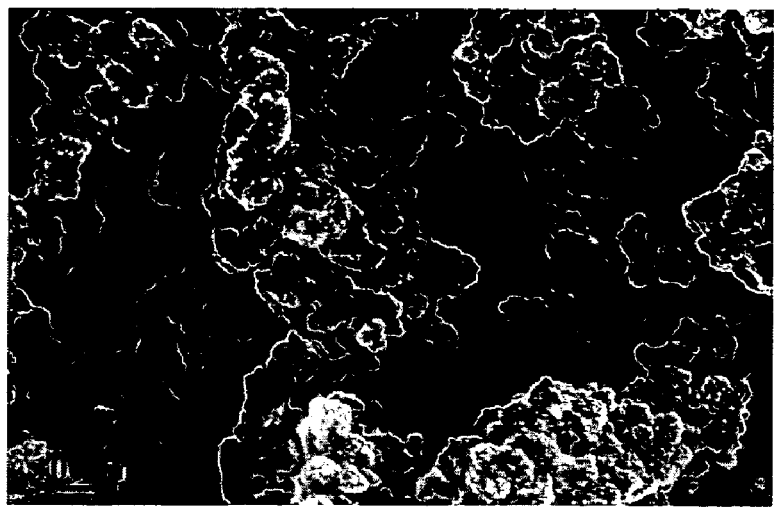
FIG. 2A is an SEM image of Ibuprofen nanoparticle samples obtained utilizing neat water as the aqueous receiving material.

FIG. 2A is an SEM analysis of the precipitate obtained when the receiving solution in the expansion chamber 18 was neat water. Initially, the aqueous suspension appeared homogeneous. Within about 15 minutes, however, the imaged precipitation appeared in the suspension.

Figure 2B:
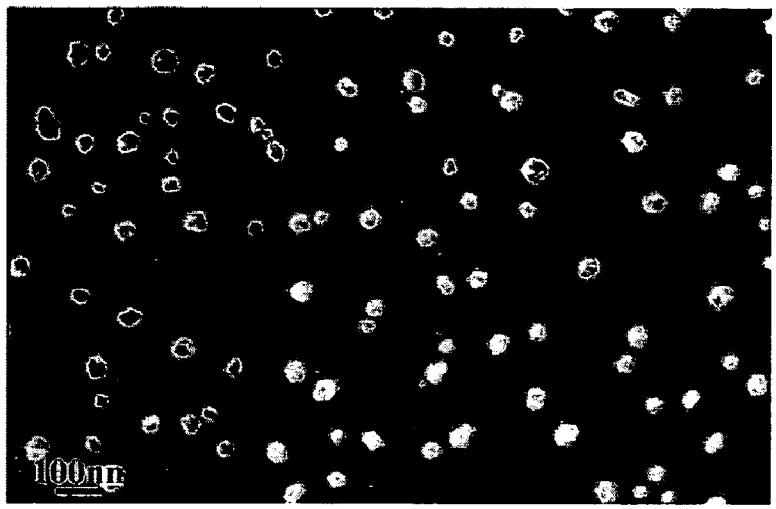
FIG. 2B is an SEM image of Ibuprofen nanoparticle samples obtained utilizing a poly(N-vinyl-2-pyrrolidone) (PVP) solution as the aqueous receiving material.

FIG. 2B is an SEM analysis of the product suspension obtained when the receiving solution included a stabilizing agent of the present invention. The receiving solution of this particular run was an aqueous solution of poly(N-vinyl-2-pyrrolidone) (PVP, available from Sigma-Aldrich Corporation, $M_w \approx 40,000$). The product suspension remained stable without precipitation for an extended period of time, with no sign of instability after several days. According to a statistical analysis of the SEM images, the nanoparticles obtained were of an average size of 40 nm in diameter, with a size distribution standard deviation of 8.5 nm.

A variation of the drug/polymer weight ratio from 0.3 to 4 resulted in no significant changes in the average particle size of the Ibuprofen nanoparticles. Increases in the loading of Ibuprofen from 0.25 to 0.83 mg/mL and in the PVP concentration from 0.5 to 3.3 mg/mL also resulted in no significant changes to the sizes of Ibuprofen nanoparticles. However, a change in the pre-expansion temperature from 40° C. to 120° C. increased the average Ibuprofen nanoparticle size from 40 nm to 52 nm. The size of the Ibuprofen nanoparticles in suspension was also found to be sensitive to changes in the molecular weight of the stabilizing agent. For example, the use of high-molecular weight PVP ($M_w \approx 360,000$) reduced the average Ibuprofen nanoparticle size to 30 nm.

Figure 2C:
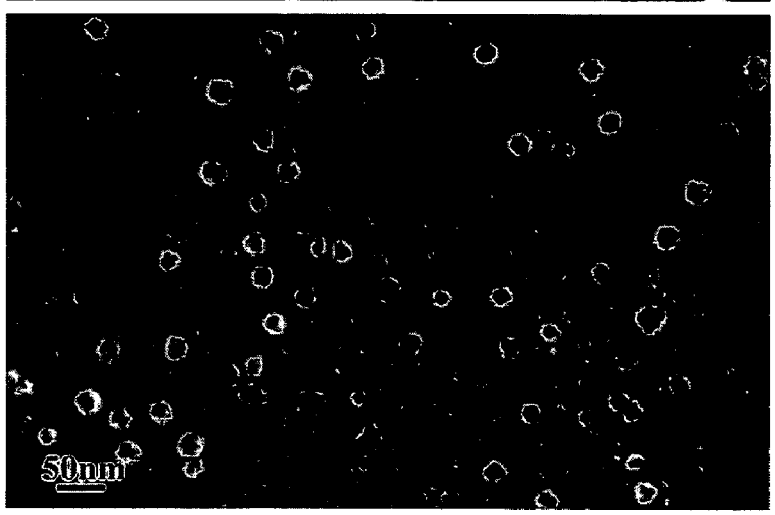
FIG. 2C is an SEM image of Ibuprofen nanoparticle samples obtained utilizing a sodium dodecyl sulfate (SDS) solution as the aqueous receiving material.

FIG. 2C is an SEM analysis of the product suspension obtained when the receiving solution included another stabilizing agent according to the present invention. The receiving solution of this particular run was an aqueous solution of sodium dodecyl sulfate (available from Sigma-Aldrich Corporation) (SDS, 3.3 mg/mL). The product suspension remained stable without precipitation. According to a statistical analysis of the SEM images, the nanoparticles obtained were of an average size of 25 nm in diameter, with a size distribution standard deviation of 5 nm.

EXAMPLE 2

Processes as described above in Example 1 were utilized to form aqueous suspensions of Naproxen particles. (Naproxen was obtained from Sigma-Aldrich Corporation.) As the solubility of Naproxen in neat supercritical $CO_2$ is relatively low, 2 wt % methanol was used as a co-solvent.

FIG. 3A is an SEM analysis of the precipitate obtained when the receiving solution in the expansion chamber 18 was neat water. Initially, the aqueous suspension appeared homogeneous. Within about 15 minutes, however, the imaged precipitation appeared in the suspension.

FIG. 3B is an SEM analysis of the product suspension obtained when the receiving solution included a stabilizing agent of the present invention. The receiving solution of this particular run was an aqueous solution of poly(N-vinyl-2-pyrrolidone) (0.5 mg/mL PVP, available from Sigma-Aldrich Corporation, $M_w \approx 40{,}000$). The product suspension remained stable without precipitation for an extended period of time, with no sign of instability after several days. According to a statistical analysis of the SEM images, the nanoparticles obtained were of an average size of 64 nm in diameter, with a size distribution standard deviation of 10 nm. Average particle size obtained appeared to be insensitive to changes in the drug/PVP weight ratio, which was varied from 0.3 to 2 in various runs.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention that is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A process comprising:

dissolving a biologically active material into a solvent to form a non-aqueous solution, wherein the biologically active material displays little or no aqueous solubility, the non-aqueous solution consisting essentially of the biologically active material and the solvent;

compressing and heating the solution to form a supercritical solution;

rapidly expanding the supercritical solution through a nozzle into an aqueous solution, wherein the aqueous solution comprises a stabilizing agent in an amount less than the critical micelle concentration of the stabilizing agent;

forming a particulate suspension in the aqueous solution, wherein the ratio of biologically active material to stabilizing agent in the particulate suspension is between 1:1 and about 4:1, wherein all of the particles formed in the aqueous suspension comprise the biologically active material, at least about 95% of the particles are less than 100 nm in size, and the particle size distribution standard deviation of all of the particles formed in the aqueous solution is less than about 15 nm.

2. The process according to claim 1, wherein the solvent is carbon dioxide.

3. The process according to claim 1, wherein the stabilizing agent is a surfactant.

4. The process according to claim 1, wherein the stabilizing agent is a food emulsifier.

5. The process according to claim 1, wherein all of the particles formed by the process have a diameter of between about 10 and about 95 nm.

6. The process according to claim 1, wherein the particle size distribution standard deviation of all of the particles formed in the aqueous solution is between about 5 and about 10 nm.

7. The process according to claim 1, wherein the ratio of the biologically active material to the stabilizing agent is between about 2:1 and about 4:1.

* * * * *